US005783737A

United States Patent [19]
Metivier

[11] Patent Number: 5,783,737
[45] Date of Patent: Jul. 21, 1998

[54] PROCESS FOR THE PREPARATION OF 3-CARBOXY-4-HYDROXYBENZALDEHIDES AND DERIVATIVES THEREOF

[75] Inventor: Pascal Metivier, Sainte Foy les Lyons, France

[73] Assignee: Rhone-Poulenc Chimie, Courbevoie, France

[21] Appl. No.: 776,343

[22] PCT Filed: May 24, 1996

[86] PCT No.: PCT/FR96/00779

§ 371 Date: Jan. 24, 1997

§ 102(e) Date: Jan. 24, 1997

[87] PCT Pub. No.: WO96/37454

PCT Pub. Date: Nov. 28, 1996

[30] Foreign Application Priority Data

May 24, 1995 [FR] France ................... 95 06186

[51] Int. Cl.$^6$ ................... C07C 45/00
[52] U.S. Cl. ................... 568/432; 568/442; 568/764
[58] Field of Search ................... 568/442, 432, 568/764

[56] References Cited

U.S. PATENT DOCUMENTS 4,351,962  9/1982  Gradeff et al. ................... 568/432

OTHER PUBLICATIONS

Eugenio et al; Farmaco et al; 46(5): 669–676, 1991.
CA vol. 52; 11776i; Cavina et al; Rend.ist.super.sanita. 18,750–765, 1955.

Jerry March; Advanced Organic Chemistry; Third Edition; p. 507, 1985.

*Primary Examiner*—Gary Geist
*Assistant Examiner*—Sreeni Padmanabhan
*Attorney, Agent, or Firm*—Katherine L. Carleton; Jean-Louis Seugnet

[57] ABSTRACT

The present invention concerns a process for the preparation of 3-carboxy-4-hydroxybenzaldehydes and derivatives thereof from phenolic compounds carrying formyl and/or hydroxymethyl groups in the 2 and 4 positions.

The invention also concerns the preparation of 4-hydroxybenzaldehydes from 3-carboxy-4-hydroxybenzaldehydes.

More particularly, the invention concerns the preparation of 3-methoxy-4-hydroxybenzaldehyde and 3-ethoxy-4-hydroxybenzaldehyde, respectively known as "vanillin" and "ethylvanillin".

The process for the preparation of 3-carboxy-4-hydroxybenzaldehyde is characterized in that the group in the 2 position in a phenolic compound carrying formyl and/or hydroxymethyl groups in the 2 and 4 positions is selectively oxidized to a carboxy group, and optionally a hydroxymethyl group in the 4 position is selectively oxidized to a formyl group.

A successive decarboxylation step for a 3-carboxy-4-hydroxybenzaldehyde produces a 4-hydroxybenzaldehyde.

29 Claims, No Drawings

PROCESS FOR THE PREPARATION OF 3-CARBOXY-4-HYDROXYBENZALDEHIDES AND DERIVATIVES THEREOF

This is the U.S. National Stage Application of PCT/FR 96/00779, filed May 24, 1996, now WO96/37454 published Nov. 28, 1996.

The present invention concerns a process for the preparation of 3-carboxy-4-hydroxybenzaldehydes and derivatives thereof from phenolic compounds carrying formyl and/or hydroxymethyl groups in the 2 and 4 positions.

The invention also concerns the preparation of 4-hydroxybenzaldehydes from 3-carboxy-4-hydroxybenzaldehydes.

More particularly, the invention concerns the preparation of 3-methoxy-4-hydroxybenzaldehyde and 3-ethoxy-4-hydroxybenzaldehyde, respectively known as "vanillin" and "ethylvanillin".

Vanillin is primarily obtained from natural sources such as lignin, but some is prepared chemically.

A number of preparation methods have been described in the literature [KIRK-OTHMER—Encyclopaedia of Chemical Technology 23, p 1710, $3^{rd}$ edition]. A number of these use guaiacol, or 2-methoxyphenol, as a starting material.

Thus, vanillin can be prepared by reacting guaiacol with glyoxylic acid, oxidising the condensate in air then liberating the vanillin from the reaction medium by acidification. The process suffers from the disadvantage that glyoxylic acid is an expensive reactant.

The Reimer-Tiemann reaction can also be used to obtain vanillin by reacting guaiacol and chloroform in the presence of potassium hydroxide. Resin formation is a disadvantage of this preparation method.

In the Gatterman reaction, vanillin is synthesised by reacting hydrogen cyanide with guaiacol in the presence of hydrochloric acid. Apart from using a reactant requiring delicate handling, that process has the disadvantage of being non-selective since vanillin formation is accompanied by isovanillin and o-vanillin formation.

A major difficulty in synthesising vanillin is selectively fixing a formyl group on the guaiacol in the position para to the hydroxy group.

A further problem is to provide a process which is industrially competitive.

The present invention provides a novel process which can overcome the above disadvantages and satisfy the requirements mentioned above.

A first object of the present invention is to provide a process for the preparation of a 3-carboxy-4-hydroxybenzaldehyde characterized in that the group in the 2 position in a phenolic compound carrying formyl and/or hydroxymethyl groups in the 2 and 4 positions is selectively oxidised to a carboxy group, and optionally a hydroxymethyl group in the 4 position is selectively oxidised to a formyl group.

A further object is to provide a preparation for a 4-hydroxybenzaldehyde using a process for the decarboxylation of a 3-carboxy4-hydroxybenzaldehyde.

The process of the invention is suitable for the preparation of vanillin. It can be used for the selective oxidation of 4,6-diformylguaiacol or 4,6-di(hydroxymethyl)guaiacol or 4-formyl-6-hydroxymethylguaiacol or 4-hydroxymethyl-6-formylguaiacol to 5-carboxy-vanillin then the elimination of the carboxy group in the 5-position to produce vanillin.

Similarly, it can be applied to guetol (2-ethoxyphenol) to produce ethylvanillin.

The process is not only selective but is also highly competitive industrially as it uses cheaper reactants.

The starting substrate used in the process of the invention is a phenolic compound carrying formyl and/or hydroxymethyl groups in the 2 and 4 positions.

The term "phenolic compound" denotes any aromatic compound with an aromatic nucleus which carries a hydroxy group.

In the following disclosure of the present invention, the term "aromatic" denotes the conventional idea of aromaticity as defined in the literature, in particular in "Advanced Organic Chemistry" by Jerry MARCH, $4^{th}$ edition, John Wiley and Sons, 1992, pp. 40 ff.

The phenolic compound has hydroxymethyl and/or formyl groups in the 2 and 4 positions.

Preferably, the phenolic compounds used in the process of the invention have the following general formula (II):

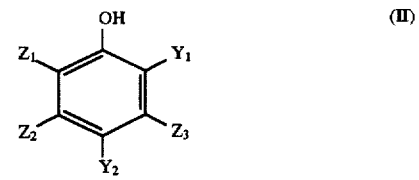

where:
- $Y_1$ and $Y_2$, which may be identical or different, represent one of the following groups:
  - a —CHO group;
  - a —CH$_2$OH group;
- $Z_1$, $Z_2$ and $Z_3$, which may be identical or different, represent a hydrogen atom, an alkyl, alkenyl, alkoxy, hydroxyalkyl, alkoxyalkyl, cycloalkyl or aryl radical, a hydroxy group, a nitro group, a halogen atom, or a trifluoromethyl group.

Particularly suitable compounds for use in the process of the invention have formula (II) where $Z_1$, $Z_2$ and $Z_3$, which may be identical or different represent one of the following atoms or groups:
- a hydrogen atom;
- a linear or branched alkyl radical containing 1 to 12 carbon atoms, preferably 1 to 4 carbon atoms, such as methyl, ethyl, propyl, isopropyl, butyl, isobutyl, sec-butyl or tert-butyl;
- a linear or branched alkenyl radical containing 2 to 12 carbon atoms, preferably 2 to 4 carbon atoms, such as vinyl or allyl;
- a linear or branched alkoxy radical containing 1 to 12 carbon atoms, preferably I to 4 carbon atoms, such as a methoxy, ethoxy, propoxy, isopropoxy, butoxy, isobutoxy, sec-butoxy or tert-butoxy radical;
- a phenyl radical;
- a halogen atom, preferably a fluorine, chlorine or bromine atom.

The present invention does not exclude the presence of substituents of different natures, provided that they do not interfere with the reactions taking place in the process of the invention.

The present invention is preferably applicable to compounds with formula (II) where $Z_1$ represents a linear or branched alkoxy radical containing 1 to 6 carbon atoms, preferably 1 to 4 carbon atoms; $Z_2$ and $Z_3$ represent a hydrogen atom; and $Y_1$ and $Y_2$ are identical and represent a formyl group or a hydroxymethyl group.

Preferred examples of substrates for use in the process of the invention are:
- 2,4-diformylphenol;
- 1,2-dihydroxy-3,5-diformylbenzene;

1-hydroxy-2-methoxy-4,6-diformylbenzene [4,6-diformylguaiacol];

1-hydroxy-2-ethoxy-4,6-diformylbenzene [4,6-diformylguetol];

4,6-di(hydroxymethyl)guaiacol;

4,6-di(hydroxymethyl)guetol.

Of the above substrates, 4,6-diformylguaiacol and 4,6-di(hydroxymethyl)guaiacol are preferable.

The process of the invention is carried out using, as the starting compound, a phenolic compound which preferably has formula (II).

A reaction scheme is given below to facilitate comprehension of the disclosure of the invention without in any way limiting the scope of the invention to the scheme.

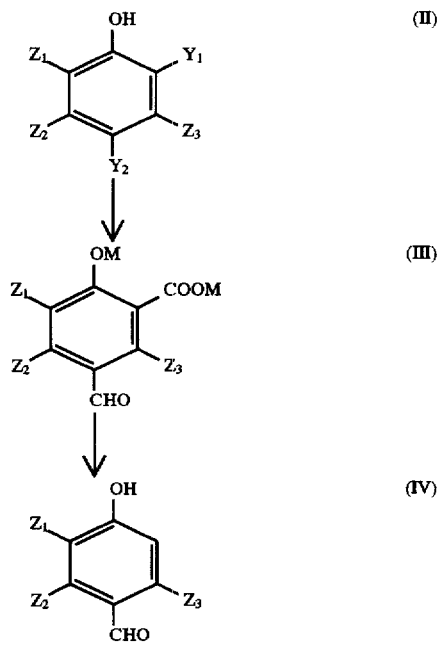

In formulae (II) to (IV):

M represents a hydrogen atom and/or a metal cation from group (Ia) or (IIa) of the periodic classification, or an ammonium cation;

$Z_1$, $Z_2$ and $Z_3$ have the meanings given above.

In the present text, references to the periodic classification of the elements are to that published in the "Bulletin de la Société de France", no. 1 (1966).

In accordance with the process of the invention, the $Y_1$ group in position 2 of a phenolic compound carrying formyl and/or hydroxymethyl groups in the 2 and 4 positions, preferably with formula (II), is selectively oxidised to a carboxy group, and optionally a hydroxymethyl group in the 4 position is selectively oxidised to a formyl group.

Oxidation is effected using molecular oxygen or a gas containing molecular oxygen, generally in the presence of a catalyst.

A preferred oxidation method consists of oxidising the phenolic compound with formula (II) in the liquid phase using molecular oxygen or a gas containing molecular oxygen, in an aqueous medium comprising a basic agent, in the presence of a catalyst based on a metal $M_1$ selected from metals from group 1b and 8 of the periodic classification of the elements, which catalyst may contain, as an activator, metals such as cadmium, cerium, bismuth, lead, silver, tellurium or tin.

We have surprisingly discovered that if the temperature is increased and the reaction is preferably carried out under pressure or if the quantity of base present during oxidation is increased, the formyl and/or hydroxymethyl groups in the 2 position are selectively oxidised to a carboxy group and the group in the 4 position is also oxidised to an aldehyde group.

The catalysts used in the process of the invention are based on a metal from group 1b and 8 of the periodic classification.

Examples of catalysts based on a metal from group 8 of the periodic classification are nickel, ruthenium, rhodium, palladium, osmium, iridium, platinum and mixtures thereof. Regarding metals from group 1b, copper is preferred.

Preferably, platinum and/or palladium catalysts are used, taken from all available forms such as: platinum black, palladium black, platinum oxide, palladium oxide or the noble metal itself deposited on different supports such as carbon black, calcium carbonate, aluminas or activated silicas or equivalent materials. Catalytic masses based on carbon black are particularly suitable.

The quantity of catalyst used, expressed as the weight of metal $M_1$ with respect to that of the phenolic compound with formula (II), can vary from 0.01% to 10%, preferably 0.04% to 2%.

Further details of the catalysts can be obtained from U.S. Pat. No. 3,673,257, and French patents FR-A-2 305 420 and FR-A-2 350 323.

The activator can be selected from all those mentioned in the above patents. Preferably, bismuth, lead and cadmium are used as the free metal or as cations. In the latter case, the associated anion is not critical and all derivatives of these metals can be used. Preferably, bismuth metal or its derivatives is used.

An inorganic or organic bismuth derivative can be used in which the bismuth atom has an oxidation number of more than zero, for example 2, 3, 4 or 5. The residue associated with the bismuth is not critical provided that is satisfies this condition. The activator can be soluble or insoluble in the reaction medium.

Illustrative examples of activators which can be used in the process of the present invention are: bismuth oxides; bismuth hydroxides; salts of inorganic hydracids such as: bismuth chloride, bromide, iodide, sulphide, selenide, or telluride; salts of inorganic oxyacids such as: bismuth sulphite, sulphate, nitrite, nitrate, phosphite, phosphate, pyrophosphate, carbonate, perchlorate, antimonate, arsenate, selenite, or selenate; and salts of oxyacids derived from transition metals such as: bismuth vanadate, niobate, tantalate, chromate, molybdate, tungstate, or permanganate.

Other suitable compounds are the salts of aliphatic or aromatic organic acids such as: bismuth acetate, propionate, benzoate, salicylate, oxalate, tartrate, lactate, or citrate; and phenates such as: bismuth gallate or pyrogallate. These salts and phenates can also be bismuthyl salts.

Other inorganic or organic compounds are binary compounds of bismuth with elements such as phosphorous or arsenic; heteropolyacids containing bismuth and salts thereof; also aliphatic and aromatic bismuthines.

Specific examples are:

oxides: BiO; $Bi_2O_3$; $Bi_2O_4$; $Bi_2O_5$;

hydroxides: $Bi(OH)_3$;

salts of inorganic hydracids: bismuth chloride $BiCl_3$; bismuth bromide $BiBr_3$; bismuth iodide $BiI_3$; bismuth sulphide $Bi_2S_3$; bismuth selenide $Bi_2Se_3$; bismuth telluride $Bi_2Te_3$;

salts of inorganic oxyacids: basic bismuth sulphite $Bi_2(SO_3)_3 \cdot Bi_2O_3 \cdot 5H_2O$; neutral bismuth sulphate $Bi_2(SO_4)_3$; bismuthyl sulphate $(BiO)HSO_4$; bismuthyl nitrite (BiO)NO$_2$.0.5H$_2$O; neutral bismuth nitrate Bi(NO$_3$)$_3$.5H$_2$O; double nitrate of bismuth and magnesium 2Bi(NO$_3$)$_3$.3Mg(NO$_3$)$_2$.24H$_2$O; bismuthyl nitrate (BiO)NO$_3$; bismuth phosphite Bi$_2$(PO$_3$H)$_3$. 3H$_2$O; neutral bismuth phosphate BiPO$_4$; bismuth pyrophosphate Bi$_4$(P$_2$O$_7$)$_3$; bismuthyl carbonate (BiO)$_2$CO$_3$;0.5H$_2$O; neutral bismuth perchlorate Bi(ClO$_4$)$_3$. 5H$_2$O; bismuthyl perchlorate (BiO)ClO$_4$; bismuth antimonate BiSbO$_4$; neutral bismuth arsenate Bi(AsO$_4$)$_3$; bismuthyl arsenate (BiO)AsO$_4$.5H$_2$O; bismuth selenite Bi$_2$(SeO$_3$)$_3$;

salts of oxyacids derived from transition metals: bismuth vanadate BiVO$_4$; bismuth niobate BiNbO$_4$; bismuth tantalate BiTaO$_4$; neutral bismuth chromate Bi$_2$(CrO$_4$); bismuthyl dichromate ([BiO]$_2$Cr$_2$O$_7$; acid bismuthyl chromate H(BiO)CrO$_4$; double chromate of bismuthyl and potassium K(BiO)CrO$_4$; bismuth molybdate Bi$_2$(MoO$_4$)$_3$; bismuth tungstate Bi$_2$(WO$_4$)$_3$; double molybdate of bismuth and sodium NaBi(MoO$_4$)$_2$; basic bismuth permanganate Bi$_2$O$_2$(OH)MnO$_4$;

salts of aliphatic or aromatic organic acids: bismuth acetate Bi(C$_2$H$_3$O$_2$)$_3$; bismuthyl propionate (BiO)C$_3$H$_5$O$_2$; basic bismuth benzoate C$_6$H$_5$CO$_2$Bi(OH)$_2$; bismuthyl salicylate C$_6$H$_4$CO$_2$(BiO)(OH); bismuth oxalate (C$_2$O$_4$)$_3$Bi$_2$; bismuth tartrate Bi$_2$(C$_4$H$_4$O$_6$)$_3$. 6H$_2$O; bismuth lactate (C$_6$H$_9$O$_5$)OBi.7H$_2$O; bismuth citrate C$_6$H$_5$O$_7$Bi;

phenates: basic bismuth gallate C$_7$H$_7$O$_7$Bi; basic bismuth pyrogallate C$_6$H$_3$(OH)$_2$(OBi)(OH).

Other inorganic or organic compounds are also suitable: bismuth phosphide BiP; bismuth arsenide Bi$_3$As$_4$; sodium bismuthate NaBiO$_3$; bismuth-thiocyanic acids H$_2$[Bi(BNS)$_5$].H$_3$[Bi(CNS)$_6$] and sodium and potassium salts thereof; trimethylbismuthine Bi(CH$_3$)$_3$, triphenylbismuthine Bi(C$_6$H$_5$)$_3$.

Preferred bismuth derivatives for use in the process of the invention are: bismuth oxides; bismuth hydroxides; bismuth or bismuthyl salts of inorganic hydracids; bismuth or bismuthyl salts of inorganic oxyacids: bismuth or bismuthyl salts of aliphatic or aromatic organic acids; and bismuth or bismuthyl phenates.

A particularly suitable group of activators for carrying out the process of the invention is constituted by bismuth oxides Bi$_2$O$_3$ and Bi$_2$O$_4$; bismuth hydroxide Bi(OH)$_3$; neutral bismuth sulphate Bi$_2$(SO$_4$)$_3$; bismuth chloride BiCl$_3$; bismuth bromide BiBr$_3$; bismuth iodide BiI$_3$; neutral bismuth nitrate Bi(NO$_3$)$_3$.5H$_2$O; bismuthyl nitrate BiO(NO$_3$); bismuthyl carbonate (BiO)$_2$CO$_3$.0.5H$_2$O; bismuth acetate Bi(C$_2$H$_3$O$_2$)$_3$; and bismuthyl salicylate C$_6$H$_4$CO$_2$(BiO)(OH).

The quantity of activator used, expressed as the quantity of metal contained in the activator with respect to the weight of metal M$_1$ used, can vary between wide limits. As an example, this quantity can be as low as 0.1% and can attain the weight of metal M$_1$ used, or even exceed it without any problems.

More particularly, this quantity is selected so that it provides the oxidation medium with 10 ppm to 900 ppm by weight of activator metal with respect to the phenolic compound with formula (II). In this respect, higher quantities of the order of 900 ppm to 1500 ppm can naturally be used, but with no great additional advantage.

In the process of the invention, oxidation is carried out in an aqueous medium containing a basic agent in solution, in particular ammonium hydroxide, alkaline or alkaline-earth bases, for example hydroxides such as sodium, potassium, lithium and -a -baryte hydroxides; alkaline alkanolates such as sodium or potassium methylate, ethylate, isopropylate or t-butylate, sodium or potassium carbonates or bicarbonates and in general, the salts of alkaline or alkaline-earth bases and weak acids.

Thus the compounds with formula (III) can be completely or partially turned into salts depending on the quantity of basic agent used. It follows that in formula (III), M symbolises a hydrogen atom and/or a metal cation from group (Ia) or (IIa), or an ammonium cation.

Sodium or potassium hydroxide is used for reasons of economy. The proportion of inorganic base to be used can be in the range 0.5 to 10 moles, preferably in the range 1 to 4 moles, and more preferably in the range 2 to 4 moles of inorganic base per mole of phenolic compound with formula (II).

The concentration by weight of phenolic compound with formula (II) in the liquid phase is usually in the range 1% to 60%, preferably in the range 2% to 30%.

In practice, one implementation of the process consists of bringing the solution comprising the phenolic compound with formula (II), the basic agent, the catalyst based on metal M$_1$, and any activator into contact with molecular oxygen or a gas containing molecular oxygen in the proportions indicated above.

Atmospheric pressure can be used, but it is preferable to use a pressure of 1 to 20 bar.

The mixture is then stirred at the desired temperature until a quantity of oxygen corresponding to that necessary to transform the hydroxymethyl group(s) and/or formyl group (s) into a carboxy group, and optionally the hydroxymethyl group into a formyl group, has been consumed.

The temperature of the reaction to be used depends on the thermal stability of the products to be prepared.

In accordance with the invention, the temperature is preferably selected so as to be in the range 30° C. to 200° C., preferably 40° C. to 160° C.

The skilled person will adapt the temperature depending on the reaction conditions (in particular the quantity of base, nature of metal M$_1$, pressure and stirring). We have discovered that the lower the temperature, the greater must be the quantity of basic agent used.

By way of example, preferred conditions for the preferred metals platinum and palladium will be given. For platinum, the temperature is between 100° C. and 160° C., and the quantity of base to be used is advantageously in the range 1 to 3 moles per mole of phenolic compound with formula (II). For palladium, the temperature can be between 30° C. and 200° C., preferably between 30° C. and 100° C., and for this latter range, the quantity of base is preferably 2 to 4 moles per mole of said phenolic compound.

At the end of the reaction, which preferably takes 30 minutes to 6 hours, 2-hydroxybenzoic acid which is formylated in the 5 position is recovered and can be partially or totally in its salt form and preferably has formula (E).

After any necessary cooling, the catalytic mass and the reaction mass are separated, for example by filtering.

In the last step of the process of the invention, a decarboxylation reaction is carried out.

This is effected by acidifying the resulting medium by adding a protonic inorganic acid, preferably hydrochloric acid or sulphuric acid or an organic acid such as trifluoromethanesulphonic acid or methanesulphonic acid, to obtain a pH of no more than 3.

The reaction medium is heated to a temperature of between 120° C. and 350° C., preferably between 150° C. and 220° C.

The process is preferably carried out under autogenous pressure of the reactants.

At the end of the reaction, the reaction medium is cooled to between 20° C. and 80° C.

A two-phase medium is obtained constituted by an organic phase comprising 4-hydroxybenzaldehyde, preferably with formula (IV) and possibly the starting substrate with formula (II), and a saline aqueous phase.

The organic and aqueous phases are separated and the 4-hydroxybenzaldehyde is recovered from the organic phase using conventional separation techniques, preferably distillation or extraction using an appropriate solvent.

In accordance with the process of the invention, a 3-carboxy-4-hydroxybenzaldehyde is obtained by selective oxidation of a phenolic compound carrying formyl and/or hydroxymethyl groups in the 2 and 4 positions.

More particularly, the starting substrates have formulae (IIa), (IIb), (IIc) and (IId) below:

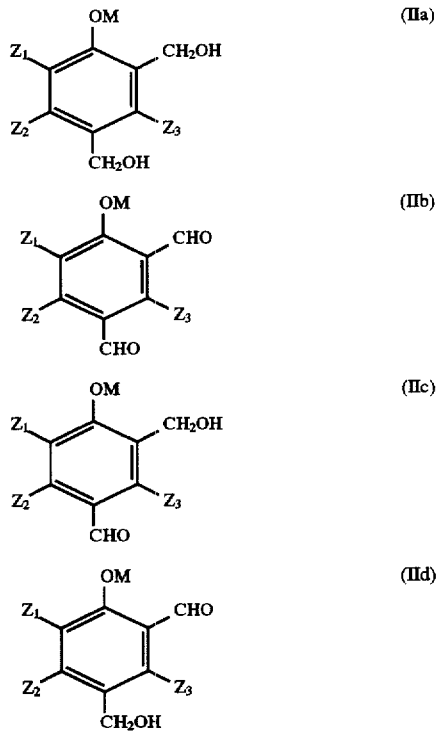

These compounds, to which the process of the invention can be applied, are known compounds which can be prepared by various organic syntheses.

Thus compounds with formula (IIb) can be prepared by oxidation of poly(hydroxymethyl)phenols with formula (IIa) with molecular oxygen or a gas containing molecular oxygen, in an aqueous alkaline phase in the presence of a catalyst based on a metal from group 8 of the periodic classification, preferably platinum or palladium, which may contain, as an activator metals, such as cadmium, cerium, bismuth, lead, silver, tellurium or tin.

Processes of this type are described in U.S. Pat. No. 3,673,257, and French patents FR-A-2 305 420 and FR-A-2 350 323.

Poly(hydroxymethyl)phenols are mainly known products which can be prepared by hydroxymethylation of substituted or unsubstituted phenols using formaldehyde or compounds which generate formaldehyde such as paraformaldehyde, under greatly different conditions: cf in particular H. G. PEER, Rec. Trav. Chim. Netherlands 79, 825–835 (1960); GB-A-774 696; GB-A-751 845; EP-A-165; J. H. FREEMAN, J. Am. Chem. Soc. 74, 6 257–6 260 (1952); and 76 2080–2087 (1954); H. G. PEER, Rec. Trav. Chim. Netherlands 78 851–863 (1959); H. EULER et al., Arkiv f ür Chem. 13, 1–7 (1939); P. CLAUS et al., Monath. Chem. 103, 1178–11293 (1972).

One phenol hydroxymethylation process which is specifically suitable for the synthesis of poly(hydroxymethyl) phenols for use in the preparation of compounds with formula (III) is the condensation of formaldehyde or formaldehyde generators with phenol in an aqueous phase in the presence of an alkaline or alkaline-earth base.

It is of particular advantage from an industrial viewpoint when using the process of the present invention to use compounds with formula (IIb) obtained by a two-step process comprising:

hydroxymethylation of a phenol in an aqueous medium in the presence of an alkaline or alkaline-earth base by formaldehyde or a formaldehyde generator to a poly(hydroxymethyl)phenol;

and oxidation, with no intermediate separation, of the poly(hydroxymethyl)phenols using molecular oxygen or a gas containing molecular oxygen in an alkaline aqueous phase in the presence of a catalyst based on a metal from group 8 of the periodic classification, and optionally a metal as described above.

More specifically again, the process of the present invention is suitable for the preparation of compounds with formula (III) from poly(hydroxymethyl)phenols with formula (IIa) obtained by a two-step process comprising:

hydroxymethylation at the ortho and para positions to the hydroxy group of an unsubstituted phenol with general formula (I):

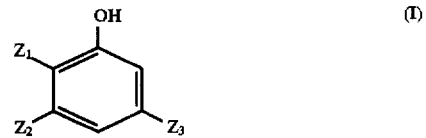

to form a poly(hydroxymethyl)phenol containing at least one hydroxymethyl group in the ortho and para position to the hydroxy group, with general formula (IIa):

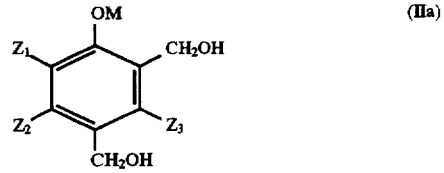

using formaldehyde or a formaldehyde generator in an aqueous phase in the presence of an alkaline or alkaline-earth base;

oxidation, in the aqueous alkaline phase, of the poly(hydroxymethyl)phenols with formula (IIa) from the first step using molecular oxygen of a gas containing molecular oxygen in the presence of a catalyst based on a metal from group 8 of the periodic classification, optionally containing a metal such as those used as an activator, without intermediate separation of poly(hydroxymethyl)phenols.

Examples of phenols with formula (I) which may act as starting points for the synthesis of compounds with formula (II) are phenol, pyrocatechin, guaiacol, guetol, 3-methoxyphenol, 3-ethoxyphenol, 3-isopropoxyphenol, 3-t-butyloxyphenol, m-cresol and o-cresol.

The conditions selected for the hydroxymethylation and oxidation of the poly(hydroxymethyl)phenols are those recommended in the prior art listed above.

Formaldehyde or any formaldehyde generator can be used, such as trioxane or paraformaldehyde used as linear paraformaldehydes of any degree of polymerisation, preferably containing 8 to 100 ($CH_2O$) units.

Formaldehyde can be used as an aqueous solution of non critical concentration. It can be in the range 20% to 50% by weight: preferably, commercial solutions are used which have a concentration of about 30% to 40% by weight.

The quantity of formaldehyde, expressed as moles of formaldehyde per mole of phenol, can vary between wide limits. The formaldehyde/phenol molar ratio can be between 1 and 8, preferably between 2 and 4.

The quantity of base present in the hydroxymethylation medium, expressed as the number of moles of base/phenolic hydroxy group of the phenol to be -hydroxymethylated, can vary between wide limits. In general, this ratio, which varies depending on the base, can be between 0.1 and 2, preferably between 0.5 and 1.1. The base used may be one of those cited above for the oxidation step. Aqueous solutions of alkaline hydroxides are particularly suitable.

In general, the hydroxymethylation step is carried out at a temperature in the range 0° C. to 100° C., preferably in the range 20° C. to 70° C.

The process is preferably carried out at a pressure which is autogenous for the reactants to avoid any paraformaldehyde losses which may be gaseous at the temperatures used.

Preferably, the reaction is carried out in a controlled atmosphere of inert gas such as nitrogen or a noble gas, for example argon.

The reaction time can vary a great deal. It is usually between 30 minutes and 24 hours, preferably between 4 hours and 8 hours.

In practice, the reaction is readily carried out by charging the phenol and formaldehyde, and any base, then stirring and heating the reaction mixture to the desired temperature for the time required to complete the reaction.

The introduction order for the reactants is not critical and can thus be different.

The oxidation of poly(hydroxymethyl)phenols to intermediate poly(formyl)phenols by molecular oxygen can be carried out as indicated above directly on the aqueous alkaline solution of salts of the poly(hydroxymethyl)phenols obtained from the hydroxymethylation step. If necessary, the pH of the solution is brought to a value in the range 8 to 13 by addition, if required, of an alkaline or alkaline-earth base. The optimal pH depends on the nature of the poly (hydroxymethyl)phenols.

The temperature of the oxidation reaction is between 10° C. and 100° C., preferably between 20° C. and 60° C.

In accordance with the invention, the phenolic compounds with formula (II) produce a 3-carboxy-4-hydroxybenzaldehyde which, after decarboxylation, produces a 4-hydroxybenzaldehyde.

As mentioned above, the process of the invention is particularly suitable for the preparation of vanillin and ethylvanillin.

Examples of implementations of the invention will be given below. These examples are given by way of illustration and are in no way limiting.

The examples describe the degree of conversion and the yield obtained.

The degree of conversion corresponds to the ratio between the number of moles of substrate transformed and the number of moles of substrate engaged.

The yield corresponds to the ratio between the number of moles of product formed and the number of moles of substrate used.

EXAMPLES

EXAMPLE 1

In this example, 4,6-diformylguaiacol was oxidised.

0.502 g of 86% 4,6-diformylguaiacol (2.41 mmole), 3.3 ml of an aqueous sodium hydroxide solution containing 33.4 g/l (2.75 mmole), 17 ml of water, 0.3 g of a catalyst containing platinum deposited on charcoal in an amount of 2.5% by weight of metal and 20 mg of bismuth sulphate [$Bi_2(SO_4)_3$] were charged into a 50 ml autoclave provided with a mechanical stirrer.

An air stream of 3 l/h was established at a pressure of 20 bar.

The reaction mixture was heated to 120° C. for 2 hours.

The reaction mixture was cooled and the pressure was returned to atmospheric pressure, then the catalyst was filtered.

The reaction medium was then analysed using high performance liquid chromatography.

The results obtained were as follows:

59% conversion of 4,6-diformylguaiacol;

59% yield of 5-carboxyvanillin.

EXAMPLE 2

In this example, 4-hydroxymethyl-6-formylguaiacol was oxidised.

0.507 g of 4-hydroxymethyl-6-formylguaiacol (2.75 mmole), 1.1 ml of an aqueous sodium hydroxide solution containing 7.69 mol/l (8.46 mmole), 19 ml of water, 0.3 g of a catalyst containing platinum deposited on charcoal in an amount of 2.5% by weight of metal and 0.0185 g of bismuth sulphate [$Bi_2(SO_4)_3$] were charged into a 50 ml autoclave provided with a mechanical stirrer.

An air stream of 3 l/h was established at a pressure of 20 bar.

The reaction mixture was heated to 45° C. for 7 hours, then 5 hours 30 at 120° C.

The reaction mixture was cooled and the pressure was returned to atmospheric pressure, then the catalyst was filtered.

The reaction medium was then analysed using high performance liquid chromatography.

The results obtained were as follows:

complete conversion of 4-hydroxymethyl-6-formylguaiacol;

52% yield of 5-carboxyvanillin;

4.5% yield of 5-carboxyvanillic acid;

29% yield of 4,6-diformylguaiacol.

EXAMPLE 3

In this example, 4-hydroxymethyl-6-formylguaiacol was oxidised.

0.507 g of 4-hydroxymethyl-6-formylguaiacol (2.75 mmole), 1.1 ml of an aqueous sodium hydroxide solution containing 7.69 mol/l (8.46 mmole), 19 ml of water, and 0.3 g of a catalyst containing platinum deposited on charcoal in an amount of 2.5% by weight of metal were charged into a 50 ml autoclave provided with a mechanical stirrer.

An air stream of 3 l/h was established at a pressure of 20 bar.

The reaction mixture was heated to 120° C. for 4 hours 30.

The reaction mixture was cooled and the pressure was returned to atmospheric pressure, then the catalyst was filtered.

The reaction medium was then analysed using high performance liquid chromatography.

The results obtained were as follows:

98% conversion of 4-hydroxymethyl-6-formylguaiacol;

25% yield of 5-carboxyvanillin;

59% yield of 4,6-diformylguaiacol.

EXAMPLE 4

In this example, 4,6-di(hydroxymethyl)guaiacol was oxidised.

0.8832 g of 75% 4,6-di(hydroxymethyl)guaiacol (3.60 mmole), 1.1 ml of an aqueous sodium hydroxide solution containing 7.69 mol/l (8.46 mmole), 19 ml of water, and 0.44 g of a catalyst containing palladium deposited on charcoal in an amount of 3% by weight of metal were charged into a 50 ml autoclave provided with a mechanical stirrer.

An air stream of 3 l/h was established at a pressure of 20 bar.

The reaction mixture was heated to 120° C. for 3 hours 40.

The reaction mixture was cooled and the pressure was returned to atmospheric pressure, then the catalyst was filtered.

The reaction medium was then analysed using high performance liquid chromatography.

The results obtained were as follows:

complete conversion of 4,6-di(hydroxymethyl)guaiacol;

32% yield of 5-carboxyvanillin;

14% yield of 4,6-diformylguaiacol;

12% yield of 5-carboxyvanillic acid.

EXAMPLE 5

In this example, 4,6-di(hydroxymethyl)guaiacol was oxidised.

0.8947 g of 75% 4,6-di(hydroxymethyl)guaiacol (3.64 mmole), 1.1 ml of an aqueous sodium hydroxide solution containing 7.69 mol/l (8.46 mmole), 19 ml of water, and 0.46 g of a catalyst containing platinum deposited on charcoal in an amount of 2.5% by weight of metal were charged into a 50 ml autoclave provided with a mechanical stirrer.

An air stream of 3 l/h was established at a pressure of 20 bar.

The reaction mixture was heated to 120° C. for 3 hours 30.

The reaction mixture was cooled and the pressure was returned to atmospheric pressure, then the catalyst was filtered.

The reaction medium was then analysed using high performance liquid chromatography.

The results obtained were as follows:

complete conversion of 4,6-di(hydroxymethyl)guaiacol;

41% yield of 5-carboxyvanillin;

31% yield of 4,6-diformylguaiacol;

4.5% yield of 5-carboxyvanillic acid.

EXAMPLE 6

In this example, vanillin was prepared using a sequence comprising oxidation of 4,6-di(hydroxymethyl)guaiacol followed by decarboxylation.

0.8952 g of 75% 4,6-di(hydroxymethyl)guaiacol (3.64 mmole), 1.1 ml of an aqueous sodium hydroxide solution containing 7.69 mol/l (8.46 mmole), 19 ml of water, and 0.44 g of a catalyst containing platinum deposited on charcoal in an amount of 2.5% by weight of metal were charged into a 50 ml autoclave provided with a mechanical stirrer.

An air stream of 3 l/h was established at a pressure of 20 bar.

The reaction mixture was heated to 120° C. for 3 hours 40.

The reaction mixture was cooled and the pressure was returned to atmospheric pressure, then the catalyst was filtered.

The reaction medium was homogeneous.

The reaction medium was then acidified using 10 ml of an aqueous 2N sulphuric acid solution.

The reaction mixture was heated under autogenous pressure for 25 min at 200° C.

The reaction medium was then cooled, diluted with acetonitrile and analysed using high performance liquid chromatography.

The vanillin yield obtained was 41%.

EXAMPLE 7

In this example, 4,6-diformylguaiacol was oxidised.

120 g of 4,6-diformylguaiacol (0.67 mole), 270 g of an aqueous sodium hydroxide solution containing 30% by weight (2 mole), 1600 ml of water, 21 g of a catalyst containing palladium deposited on charcoal in an amount of 3% by weight of metal and 1.4 g of bismuth sulphate [$Bi_2(SO_4)_3$] were charged into a 2000 ml autoclave provided with a mechanical stirrer.

An air stream of 600 l/h was established at a pressure of 15 bar.

The reaction mixture was heated to 100° C. for 1 hour.

The reaction mixture was cooled and the pressure was returned to atmospheric pressure, then the catalyst was filtered.

The reaction medium was then analysed using high performance liquid chromatography.

The results obtained were as follows:

84% conversion of 4,6-diformylguaiacol;

82% yield of 5-carboxyvanillin;

EXAMPLE 8

In this example, 4,6-diformylguaiacol was again oxidised.

120 g of 4,6-diformylguaiacol (0.67 mole), 210 g of an aqueous sodium hydroxide solution containing 30% by weight (2 mole), 1650 ml of water, 20 g of a catalyst containing platinum deposited on charcoal in an amount of 3% by weight of metal and 0.3 g of bismuth sulphate [$Bi_2(SO_4)_3$] were charged into a 2000 ml autoclave provided with a mechanical stirrer.

An air stream of 600 l/h was established at a pressure of 15 bar.

The reaction mixture was heated to 140° C. for 3 hours.

The reaction mixture was cooled and the pressure was returned to atmospheric pressure, then the catalyst was filtered.

The reaction medium was then analysed using high performance liquid chromatography.

The results obtained were as follows:

89% conversion of 4,6-diformylguaiacol;

81% yield of 5-carboxyvanillin;

What is claimed is:

1. A process for the preparation of a 3-carboxy-4-hydroxybenzaldehyde comprising the step of selectively oxidizing to a carboxy group the group in the 2 position of a phenol compound carrying formyl or hydroxymethyl groups in the 2 and 4 positions, and, optionally, selectively oxidizing a hydroxymethyl group in the 4 position to a formyl group.

2. A process according to claim 1, wherein the phenolic compound has general formula (II):

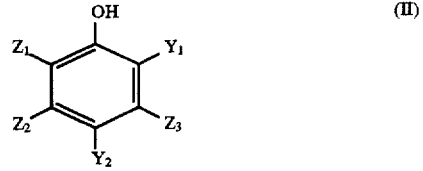

wherein:
   $Y_1$ and $Y_2$, identical or different, represent a —CHO group or a —CH$_2$OH group; and
   $Z_1$, $Z_2$ and $Z_3$, identical or different, are selected from the group consisting of a hydrogen atom, an alkyl, alkenyl, alkoxy, hydroxyalkyl, alkoxyalkyl, cycloalkyl, aryl radical, a hydroxy group, a nitro group, a halogen atom, and a trifluoromethyl group.

3. A process according to claim 2, wherein $Z_1$, $Z_2$, and $Z_3$, identical or different, are selected from the group consisting of:
   a hydrogen atom;
   a linear or branched alkyl radical containing 1 to 12 carbon atoms;
   a linear or branched alkenyl radical containing 2 to 12 carbon atoms;
   a linear or branched alkoxy radical containing 1 to 12 carbon atoms;
   a phenyl radical; and
   a halogen atom.

4. A process according to claim 2, wherein $Z_1$ represents a linear or branched alkoxy radical containing 1 to 6 carbon atoms; $Z_2$ and $Z_3$ represent a hydrogen atom; and $Y_1$ and $Y_2$ are identical and represent a formyl group or a hydroxymethyl group.

5. A process according to claim 1, wherein the phenolic compound is selected from the group consisting of:
   2,4-diformylphenol;
   1,2-dihydroxy-3,5-diformylbenzene;
   1-hydroxy-2-methoxy-4,6-diformylbenzene [4,6-diformylguaiacol];
   1-hydroxy-2-ethoxy-4,6-diformylbenzene [4,6-diformylguetol];
   4,6-di(hydroxymethyl)guaiacol; and
   4,6-di(hydroxymethyl)guetol.

6. A process according to claim 1, wherein the phenolic compound is oxidized in a liquid phase using molecular oxygen or a gas containing molecular oxygen, in an aqueous medium comprising a basic agent, in the presence of a catalyst based on a metal $M_1$ selected from the group consisting of metals from group 1b and 8 of the periodic classification of the elements, which catalyst optionally further contains, as an activator, a metal.

7. A process according to claim 6, wherein the metal activator is selected from the group consisting of cadmium, cerium, bismuth, lead, silver, tellurium or tin.

8. A process according to claim 6, wherein the catalyst is based on copper, nickel, ruthenium, rhodium, palladium, osmium, iridium, platinum or mixtures thereof.

9. A process according to claim 8, wherein the platinum or palladium catalyst is provided in the form of platinum black, palladium black, platinum oxide, palladium oxide or the metal itself deposited on supports selected from the group consisting of carbon black, calcium carbonate, aluminas and activated silicas.

10. A process according to claim 6, wherein the quantity of catalyst used, expressed as the weight of metal $M_1$ with respect to that of the phenolic compound, is from 0.01% to 10%.

11. A process according to claim 6, wherein the activator is an organic or inorganic derivative of bismuth selected from the group consisting of bismuth oxides; bismuth hydroxides; bismuth salts of inorganic hydracids; bismuthyl salts of inorganic hydracids; bismuth salts of inorganic oxyacids; bismuthyl salts of inorganic oxyacids; bismuth salts of aliphatic or aromatic organic acids; bismuthyl salts of aliphatic or aromatic organic acids; bismuth phenates; and bismuthyl phenates.

12. A process according to claim 11, wherein the bismuth derivative is selected from the group consisting of bismuth oxides $Bi_2O_3$ and $Bi_2O_4$; bismuth hydroxide $Bi(OH)_3$; bismuth chloride $BiCl_3$; bismuth bromide $BiBr_3$; bismuth iodide $BiI_3$; neutral bismuth sulphate $Bi_2(SO_4)_3$; neutral bismuth nitrate $Bi(NO_3)_3.5H_2O$; bismuthyl nitrate $BiO(NO_3)$; bismuthyl carbonate $(BiO)_2CO_3.0.5H_2O$; bismuth acetate $Bi(C_2H_3O_2)_3$, and bismuth salicylate $C_6H_4CO_2(BiO)OH$.

13. A process according to claim 12, wherein the quantity of activator is selected so that the medium contains at least 0.1% by weight of metal activator with respect to the weight of metal $M_1$ used, and 10 to 900 ppm by weight of metal $M_1$ with respect to the phenolic compound.

14. A process according to claim 6, wherein the oxidation reaction is carried out within a temperature range of 30° C. to 200° C.

15. A process according to claim 1, wherein a pressure of 1 to 20 bar is used.

16. A process according to claim 1, wherein the oxidation is carried out in an aqueous medium containing, in solution, a basic agent, in a quantity such that it represents 0.5 to 10 moles of inorganic base per mole of phenolic compound.

17. A process according to claim 16 wherein the basic agent is sodium or potassium hydroxide.

18. A process according to claim 17, wherein the phenolic compound is 2-hydroxybenzoic acid formylated in the 5 position and which is decarboxylated and optionally partially or completely in the form of its salt.

19. A process according to claim 18, wherein the 2-hydroxybenzoic acid formylated in the 5 position has the following general formula (III):

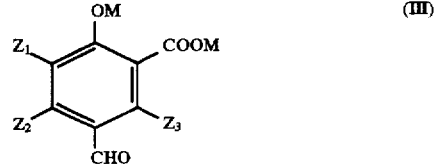

wherein:
   M represents a hydrogen atom, a metal cation from group (Ia) or (IIa) of the periodic classification, or an ammonium cation; and
   $Z_1$, $Z_2$ and $Z_3$, identical or different, are selected from the group consisting of a hydrogen atom, an alkyl, alkenyl, alkoxy, hydroxyalkyl, alkoxyalkyl, cycloalkyl, aryl radical, a hydroxy group, a nitro group, a halogen atom, and a trifluoromethyl group.

20. A process according to claim 18, wherein the acid is decarboxylated by addition of a protonic acid of inorganic origin until a pH of no more than 3 is attained.

21. A process according to claim 18, wherein the reaction medium is heated to a temperature between 120° C. and 350° C., and after cooling, the 4-hydroxybenzaldehyde is separated which has the following formula (IV):

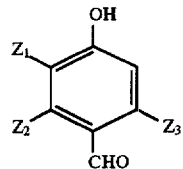

where:
Z₁, Z₂ and Z₃, identical or different, are selected from the group consisting of a hydrogen atom, an alkyl, alkenyl, alkoxy, hydroxyalkyl, alkoxyalkyl, cycloalkyl, aryl radical, a hydroxy group, a nitro group, a halogen atom, and a trifluoromethyl group.

22. A process according to claim 1, wherein the phenolic compound has formulae (IIa), (IIb), (IIc) or (IId):

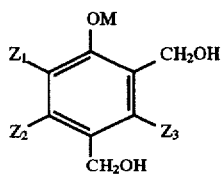

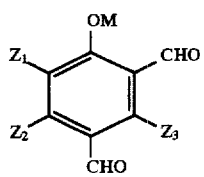

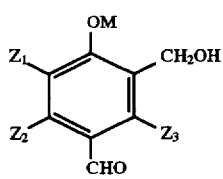

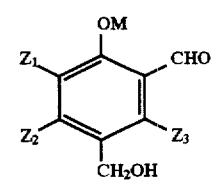

wherein:
M represents a hydrogen atom, a metal cation from group (Ia) or (IIa) of the periodic classification, or an ammonium cation;
Z₁, Z₂ and Z₃ identical or different, are selected from the group consisting of a hydrogen atom, an alkyl, alkenyl, alkoxy, hydroxyalkyl, alkoxyalkyl, cycloalkyl, aryl radical, a hydroxy group, a nitro group, a halogen atom, and a trifluoromethyl group.

23. A process according to claim 22, wherein the compound with formula (IIb) is prepared by oxidation of a poly(hydroxymethyl)phenol with formula (IIa) by molecular oxygen or a gas containing molecular oxygen, in an aqueous alkaline phase in the presence of a catalyst based on a metal from group 8 of the periodic classification, optionally containing, as an activator, a metal selected from the group consisting of cadmium, cerium, bismuth, lead, silver, tellurium or tin.

24. A process according to claim 23, wherein the poly (hydroxymethyl)phenol with formula (Ia) is obtained by a two-step process comprising:
hydroxymethylation at the ortho and para positions to the hydroxy group of an unsubstituted phenol with general formula (I):

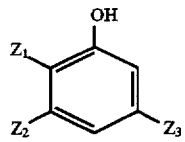

to form a poly(hydroxymethyl)phenol containing at least one hydroxymethyl group in the ortho and para position to the hydroxy group, with general formula (IIa):

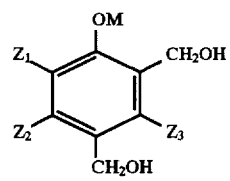

using formaldehyde or a formaldehyde generator in an aqueous phase in the presence of an alkaline or alkaline-earth base; and
oxidation, in the aqueous alkaline phase, of the poly (hydroxymethyl)phenols with formula (IIa) from the first step using molecular oxygen or a gas containing molecular oxygen in the presence of a catalyst based on a metal from group 8 of the periodic classification, optionally containing a metal activator, without intermediate preparation of poly(hydroxymethyl)phenols.

25. A process according to claim 24, wherein the phenol with formula (I) is selected from the group consisting of phenol, pyrocatechin, guaiacol, guetol, 3-methoxyphenol, 3-ethoxyphenol, 3-isopropoxyphenol, 3-t-butyloxyphenol, m-cresol, and o-cresol.

26. A process according to claim 24, wherein the reaction oxidation of compounds with formula (IIa) is carried out within a temperature range of 10° C. to 100° C.

27. A process for the preparation of a 4-hydroxybenzaldehyde comprising the steps of decarboxylation of a 3-carboxy-4-hydroxybenzaldehyde, wherein the 3-carboxy-4-hydroxybenzaldehyde is obtained by subjecting a phenolic compound carrying formyl or hydroxymethyl groups in the 2 and 4 positions to selective oxidation of the group in the 2 position to a carboxylic group, and optionally of a hydroxymethyl group in the 4 position to a formyl group, using the process according to claim 1.

28. A process for the preparation of vanillin comprising the steps of: a compound selected from the group consisting of 4,6-diformylguaiacol, 4,6-di(hydroxymethyl)guaiacol, 4-formyl-6-hydroxymethylguaiacol and 4-hydroxymethyl-6-formylguaiacol is oxidized to 5-carboxy-vanillin using the process according to claim 1, then the carboxy group in the 5 position is eliminated to produce vanillin.

29. A process for the preparation of ethylvanillin comprising the steps of: a compound selected from the group consisting of 4,6-diformylguetol, 4,6-di(hydroxymethyl) guetol, 4-formyl-6-hydroxymethylguetol and 4-hydroxymethyl-6-formylguetol is oxidized to 5-carboxyethylvanillin using the process described in claim 1, then the carboxy group in the 5 position is eliminated to produce ethylvanillin.

* * * * *